Feb. 16, 1965 HIROSHI MIYAWAKI Plant Pat. 2,473
ROSE PLANT
Filed Dec. 27, 1963
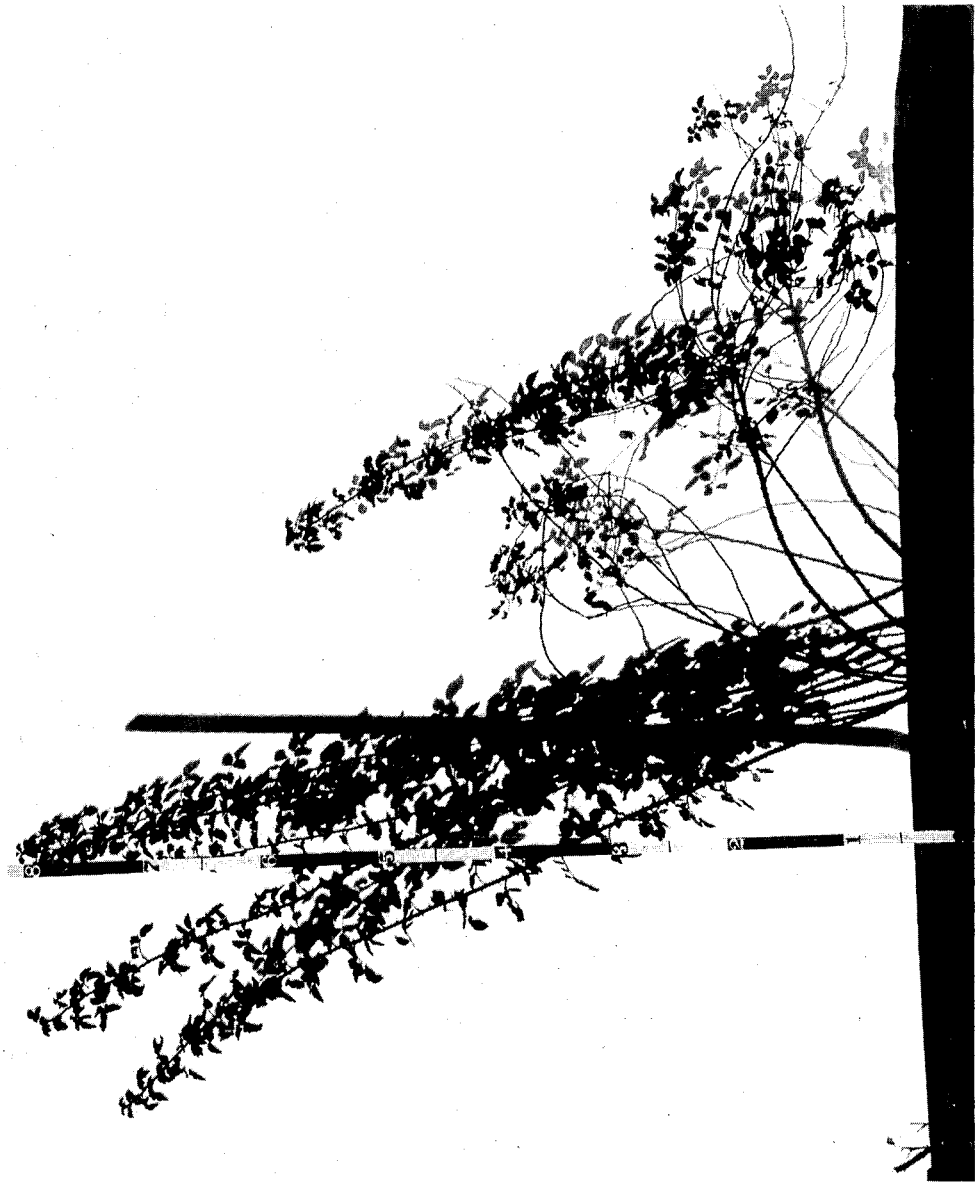
Inventor.
Hiroshi Miyawaki
By: Robb & Robb
Attorneys United States Patent Office Plant Pat. 2,473
Patented Feb. 16, 1965

2,473
ROSE PLANT

Hiroshi Miyawaki, Hiroshima, Japan, assignor to Armstrong Nurseries, Inc., Ontario, Calif., a corporation of California Filed Dec. 27, 1963, Ser. No. 334,065
1 Claim. (Cl. Plt.—5)

The present invention relates to a new and distinct variety of rose plant of the climber class, which originated as a bud sport of the variety known as "Sterling Silver" (U.S. Plant Patent No. 1,433), but which is definitely distinguished from the parent variety by its climbing habit of growth.

This new variety was discovered by me in my cultivated garden in Hiroshima, Japan, where I was growing plants of the regular bush variety "Sterling Silver." At the time of my discovery of the new variety, my attention was attracted to one of the "Sterling Silver" plants from which there had sprung a climbing cane. Upon close examination of this plant, I found that it had sported and I thereupon promptly took steps to preserve the sport, keep it under observation, and to asexually reproduce the same for the purpose of determining whether its climbing habit was fixed and transmissible by asexual reproduction. As the result, the climbing habit was fully confirmed by plants asexually reproduced by me by grafting, as performed in Japan, and also as performed on my behalf at Ontario, California, U.S.A.

The parent variety "Sterling Silver" is a popular rose variety of the regular bush type and of the hybrid tea class, but so far as I am aware, it has never previously exhibited a climbing habit, and its growth has been that of the average bush rose.

The new variety herein is substantially identical in all respects to its parent, except that it is definitely a climber, as evidenced by its long, strong canes which attain a mature height of usually 8 feet to 10 feet. Like most climbing sports of other bush varieties, the new variety produces few or no flowers on the current season's growth. Rarely, a climbing cane will terminate in a flower or small cluster of flowers, or a cane originating early in the season will produce a few lateral flowering shoots late in the season. This is a marked distinction from the relatively continuous blooming or ever-blooming habit from current season's wood which is characteristic of the bush form of the parent variety "Sterling Silver."

In view of the general similarities between my new variety and its parent, except as noted in the foregoing, it is unnecessary to specifically describe or illustrate the new variety in detail herein, since it otherwise substantially conforms to the detailed description and illustration embodied in U.S. Plant Patent No. 1,433, issued November 8, 1955, to which reference may be readily had. However, for convenience, the accompanying drawing has been presented to illustrate the climbing habit of growth of my new variety.

I claim:

A new and distinct variety of rose plant of the climber class, substantially as herein shown and described, characterized particularly as to novelty by being substantially identical with its parent variety "Sterling Silver" (U.S. Plant Patent No. 1,433), but being essentially distinguished therefrom by its long and strong canes which attain a mature height of from 8 feet to 10 feet, indicative of its climbing habit, and the habit of producing few or no flowers on the current season's growth.

No references cited.

ABRAHAM G. STONE, *Primary Examiner.*